US007869020B1

(12) United States Patent
Lee (10) Patent No.: US 7,869,020 B1
(45) Date of Patent: Jan. 11, 2011

(54) FOURIER FILTERS, INSPECTION SYSTEMS, AND SYSTEMS FOR FABRICATING FOURIER FILTERS

(75) Inventor: Shing Lee, Fremont, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 757 days.

(21) Appl. No.: 11/683,554

(22) Filed: Mar. 8, 2007

(51) Int. Cl.
*G01N 21/00* (2006.01)
(52) U.S. Cl. ............... 356/237.1; 356/239.1; 356/445; 356/239.3
(58) Field of Classification Search ... 356/237.1–237.6, 356/432, 445, 239.3, 239.1
See application file for complete search history.

(56) References Cited

U.S. PATENT DOCUMENTS 6,020,957 A * 2/2000 Rosengaus et al. ....... 356/237.4
7,307,714 B2 * 12/2007 Cyr et al. ............... 356/239.1
2007/0247668 A1 * 10/2007 Fuchs et al. ............ 382/210

OTHER PUBLICATIONS

U.S. Appl. No. 11/464,567, filed Aug. 15, 2006, Chen et al.

* cited by examiner

*Primary Examiner*—Gregory J Toatley
*Assistant Examiner*—Iyabo S Alli
(74) *Attorney, Agent, or Firm*—Ann Marie Mewherter (57) ABSTRACT

Fourier filters, inspection systems, and systems for fabricating Fourier filters are provided. One Fourier filter configured for use in an inspection system includes a substrate that is substantially transparent to light from a specimen illuminated by the inspection system. The Fourier filter also includes an array of patterned features formed on the substrate. The patterned features are formed of one or more pigments on the substrate. The patterned features are configured to block light reflected and diffracted from structures on the specimen and to allow light scattered from defects on the specimen to pass through the substrate.

31 Claims, 4 Drawing Sheets

Fig. 8 the wafer during, or as a result of, processing. Therefore, inspecting patterned wafers or product wafers may provide more accurate monitoring and control of processes and process tools than inspection of monitor wafers.

FOURIER FILTERS, INSPECTION SYSTEMS, AND SYSTEMS FOR FABRICATING FOURIER FILTERS

BACKGROUND OF THE INVENTION

1. Field of the Invention

This invention generally relates to Fourier filters, inspection systems, and systems for fabricating Fourier filters. Certain embodiments relate to a Fourier filter that includes an array of patterned features formed of one or more pigments on a substrate and configured to block light reflected and diffracted from structures on a specimen and to allow light scattered from defects on the specimen to pass through the substrate.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Many different types of inspection tools have been developed for the inspection of semiconductor wafers. Defect inspection is currently performed using techniques such as bright field (BF) imaging, dark field (DF) imaging, and scattering. The type of inspection tool that is used for inspecting semiconductor wafers may be selected based on, for example, characteristics of the defects of interest and characteristics of the wafers that will be inspected. For example, some inspection tools are designed to inspect unpatterned semiconductor wafers or patterned semiconductor wafers.

Inspection tools for unpatterned wafers are generally not capable of inspecting patterned wafers for a number of reasons. For example, many unpatterned wafer inspection tools are configured such that all of the light collected by a lens or another collector is directed to a single detector that generates a single output signal representative of all of the collected light. Therefore, light scattered from patterns or other features on the specimen will be combined with other scattered light. As such, light scattered from patterns or other features on the wafer cannot be detected separately from other scattered light thereby hindering, if not preventing, defect detection.

Patterned wafer inspection is of particular interest and importance to the semiconductor industry because processed semiconductor wafers usually have a pattern of features formed thereon. Although inspection of unpatterned wafers, or "monitor wafers," which have been run through a process tool, may be used as a gauge for the number and types of defects that may be found on patterned wafers, or "product wafers," defects detected on monitor wafers do not always accurately reflect the defects that are detected on patterned wafers after the same process in the same process tool. Inspection of patterned wafers is, therefore, important to accurately detect defects that may have been formed on the wafer during, or as a result of, processing. Therefore, inspecting patterned wafers or product wafers may provide more accurate monitoring and control of processes and process tools than inspection of monitor wafers.

Many inspection tools have been developed for patterned wafer inspection. Some patterned wafer inspection tools utilize spatial filters to separate light scattered from patterned features from other scattered light such that the other scattered light may be separately detected. Since the light scattered from patterned features depends on various characteristics of the patterned features such as lateral dimension and period, the design of the spatial filter also depends on such characteristics of the patterned features. As a result, the spatial filter must be designed based on known or determined characteristics of the patterned features and must vary as different patterned features are being inspected.

One type of spatial filter that may be used as described above is a Fourier filter. Fourier filters are relatively useful for filtering light from repetitive patterns such as memory arrays formed on a wafer. At least two previous methods have been used for Fourier filtering. One method is a mechanical method. This method utilizes mechanical rods or other mechanical devices to block the diffraction pattern generated by array structures so that the energy from the array region is removed from the optical path of the inspection system. Another method is a liquid crystal method. This method utilizes a one-dimensional or two-dimensional liquid crystal device to block the diffraction pattern generated by array structures so that the energy from the array region is removed from the optical path of the inspection system.

Although the above Fourier filtering methods have been relatively widely used, these methods do have a number of significant disadvantages. For example, the mechanical method has a number of disadvantages, particularly for flood illumination based systems. In particular, the diffraction peaks for flood illumination based systems are dots. Mechanical rods, therefore, block excessive amounts of light in such systems thereby reducing the overall defect signals. In addition, the mechanical method induces significantly more Fourier filter ringing that causes periphery energy leakage in output generated during inspection of the array region thereby reducing defect sensitivities in the array region. In particular, Fourier filters in the form of periodic blocking bars can diffract light into undesirable directions, which is commonly referred to as ringing or side lobes, thereby degrading the imaging quality. Therefore, the Fourier filter can produce significant distortion at the image plane, which adversely affects the ability of the inspection system to detect defects on the wafer with high accuracy. Furthermore, since the rods must have a relatively large diameter in order to be structurally sound, only a limited number of rods can be used. Otherwise, the entire plane would be blocked by the rods.

Currently used liquid crystal Fourier filter devices are programmable and capable of filtering out diffraction dots in a two-dimensional manner. However, there are several factors that make the liquid crystal devices inappropriate for flood illumination based systems. For example, the use of a liquid crystal device as a Fourier filter utilizes the principle of light scattering. For a flood illumination based system, the light scattering significantly alters the wavefront of the system thereby causing severe degradation to the image quality. In addition, most liquid crystal material has a damage threshold at a wavelength of approximately 300 nm thereby making liquid crystal devices less than ideal for use in deep ultraviolet (DUV) based systems (i.e., systems that operate at wavelength(s) less than about 300 nm).

Chrome masks may also be used as Fourier filters. Chrome masks generally include opaque chrome regions arranged in a pattern on a substantially transparent substrate. Therefore, chrome mask Fourier filters are similar in structure to binary masks used for patterning a resist in a lithography process. Chrome mask Fourier filters can also be fabricated using a process similar to a reticle manufacturing process. For example, a chrome mask Fourier filter may be fabricated by depositing chrome on the substrate, patterning the chrome by lithography and etch, and cleaning the substrate with the patterned chrome formed thereon. Some disadvantages of using chrome masks for Fourier filters are the relatively long turn around time and relatively high costs associated with fabricating such Fourier filters. In particular, since the chrome masks are generally made with lithography and cleaning steps, fabricating such Fourier filters is time consuming and expensive. In addition, a dedicated lithography and cleaning station in the semiconductor fabrication facility ("fab") for fabricating Fourier filters is not practical. However, designing a mask and sending the design out for fabrication would cause several days of down time for the inspection system, which is also not practical.

Micro-electro-mechanical system (MEMS) devices may also be used for Fourier filtering. MEMS devices have been proposed for Fourier filtering, at least in part, due to their programmable features. However, there is some difficulty associated with using MEMS devices for Fourier filtering. For example, using MEMS devices for Fourier filtering may be difficult due to the fill factor of the MEMS devices, which needs to be more than about 99%, the surface roughness, which needs to be less than about 2 nm for reflection mode, the pixel edge diffraction of the MEMS devices, and the pixel stability and wave front error of the MEMS devices. Advances have been made to address the fill factor of MEMS devices (e.g., with pixels having sizes of, for example, about 20 µm×about 400 µm) and wave front error of the MEMS devices (e.g., using a corrector plate) as described in commonly assigned U.S. patent application Ser. No. 11/464,567 by Chen et al. filed Aug. 16, 2006, which is incorporated by reference as if fully set forth herein. However, the use of relatively long pixels may create new process issues for MEMS device manufacturing, and relatively large area blockage on the long pixel side to accommodate design tolerance may present a new difficulty associated with using MEMS devices as Fourier filters. Whether each of these risks can be mitigated remains to be seen.

Accordingly, it would be advantageous to develop a system configured to inspect a specimen that includes a two-dimensional Fourier filter suitable for flood illuminated DF wafer inspection systems, which does not block excessive amounts of light such that the overall defect signals are not reduced, does not induce significant Fourier filter ringing and periphery energy leakage, does not significantly alter the wavefront of the system, does not cause degradation of the image, is structurally sound, and is suitable for use at DUV and other wavelengths.

SUMMARY OF THE INVENTION

The following description of various Fourier filter and system embodiments is not to be construed in any way as limiting the subject matter of the appended claims.

One embodiment relates to a Fourier filter configured for use in an inspection system. The Fourier filter includes a substrate that is substantially transparent to light from a specimen illuminated by the inspection system. The Fourier filter also includes an array of patterned features formed on the substrate. The patterned features are formed of one or more pigments on the substrate. The patterned features are configured to block light reflected and diffracted from structures on the specimen and to allow light scattered from defects on the specimen to pass through the substrate.

In some embodiments, the one or more pigments include ink printed on the substrate. In one embodiment, an area of the specimen illuminated by the inspection system includes a two-dimensional field of view of the specimen. In another embodiment, the light from the specimen includes deep ultraviolet (DUV) light. In an additional embodiment, the inspection system is configured as a dark field inspection system. In a further embodiment, the specimen is illuminated by the inspection system with coherent illumination. In a different embodiment, the specimen is illuminated by the inspection system with incoherent illumination.

In one embodiment, the array of patterned features includes a two-dimensional array of the patterned features. In another embodiment, the patterned features include anodized patterned features. In some embodiments, the patterned features have rough edges. In an additional embodiment, the patterned features have a length of about 0.1 mm to about 2 mm and a width of about 0.1 mm to about 2 mm. In a further embodiment, each of the patterned features is formed of multiple spots of the one or more pigments.

In one embodiment, the light blocked by the patterned features includes light reflected and diffracted from structures on the specimen having different diffraction patterns. In another embodiment, the Fourier filter includes an additional array of patterned features formed on the substrate. In one such embodiment, the patterned features of the additional array are configured to block light reflected and diffracted from structures on a different specimen and to allow light scattered from defects on the different specimen to pass through the substrate.

In one embodiment, the substrate is formed of a substantially transparent material, and the substantially transparent material includes fused silica, calcium fluoride, or magnesium fluoride. In one embodiment, the Fourier filter includes one or more anti-reflection coatings formed on both sides of the substrate. In another embodiment, the Fourier filter includes one or more anti-reflection coatings fowled on the substrate under the array of the patterned features.

In another embodiment, the one or more pigments include one or more pigments that are curable by ultraviolet (UV) light. In one embodiment, the one or more pigments exhibit substantially no outgassing after being cured by light. In another embodiment, the one or more pigments exhibit substantially no outgassing without being cured by light. In an additional embodiment, the one or more pigments exhibit substantially no outgassing when illuminated by the light from the specimen. Each of the embodiments of the Fourier filter described above may be further configured as described herein.

Another embodiment relates to a system configured to inspect a specimen. The system includes an illumination subsystem configured to illuminate a two-dimensional field of view on the specimen. The system also includes a collection subsystem configured to collect light from the specimen. In addition, the system includes a Fourier filter positioned at a Fourier plane of the collection subsystem. The Fourier filter includes a substrate that is substantially transparent to the light from the specimen and an array of patterned features formed on the substrate. The patterned features are formed of one or more pigments on the substrate. The patterned features are configured to block light reflected and diffracted from structures on the specimen and to allow light scattered from defects on the specimen to pass through the substrate. The system further includes a detection subsystem configured to generate output responsive to the light that passes through the substrate. The output can be used to detect the defects on the specimen.

In one embodiment, the system includes a control subsystem configured to align the Fourier filter in the Fourier plane by translating the Fourier filter within the Fourier plane until an intensity measured by the detection subsystem is minimized. Each of the embodiments of the system described above may be further configured as described herein.

An additional embodiment relates to a system configured to fabricate a Fourier filter for use in an inspection system. This system includes an optical subsystem configured to generate an image of light in a Fourier plane of the inspection system. The light is reflected and diffracted from structures on a specimen. The system also includes a fabrication subsystem configured to form an array of patterned features on a substrate with one or more pigments to thereby fabricate the Fourier filter. The substrate is substantially transparent to light from the specimen. In addition, the system includes a control subsystem configured to control the fabrication subsystem based on the image generated by the optical subsystem such that the patterned features fanned on the substrate block the light reflected and diffracted from the structures on the specimen and allow light scattered from defects on the specimen to pass through the substrate.

In some embodiments, the fabrication subsystem includes a print head configured to form the array of the patterned features on the substrate. In one embodiment, the fabrication subsystem is configured to form drops of the one or more pigments having a size of greater than about 500 dpi. In another embodiment, the one or more pigments include one or more pigments that are curable by UV light.

In one embodiment, the system includes a mask having known features formed thereon. In one such embodiment, the control subsystem is configured to calibrate the optical subsystem using the mask prior to imaging of the light in the Fourier plane. In another embodiment, the light in the Fourier plane imaged by the optical subsystem includes light reflected and diffracted from all structures formed on the specimen. In one such embodiment, the control subsystem is configured to control the fabrication subsystem based on the image generated by the optical subsystem, diffraction orders of interest, a calibration factor, and tolerances of diffraction width.

In some embodiments, the control subsystem is configured to control the fabrication subsystem to cause the patterned features to have apodization. In another embodiment, the control subsystem is configured to control the fabrication subsystem to cause the patterned features to have rough edges. Each of the embodiments of the system described above may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" refers to a reticle or a wafer. The terms "reticle" and "mask" are used interchangeably herein. A reticle generally includes a transparent substrate such as glass, borosilicate glass, and fused silica having opaque regions formed thereon in a pattern. The opaque regions may be replaced by regions etched into the transparent substrate. Many different types of reticles are known in the art, and the term reticle as used herein is intended to encompass all types of reticles.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features or periodic structures. Formation and processing of such layers of material may ultimately result in completed devices. Many different types of devices may be fowled on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
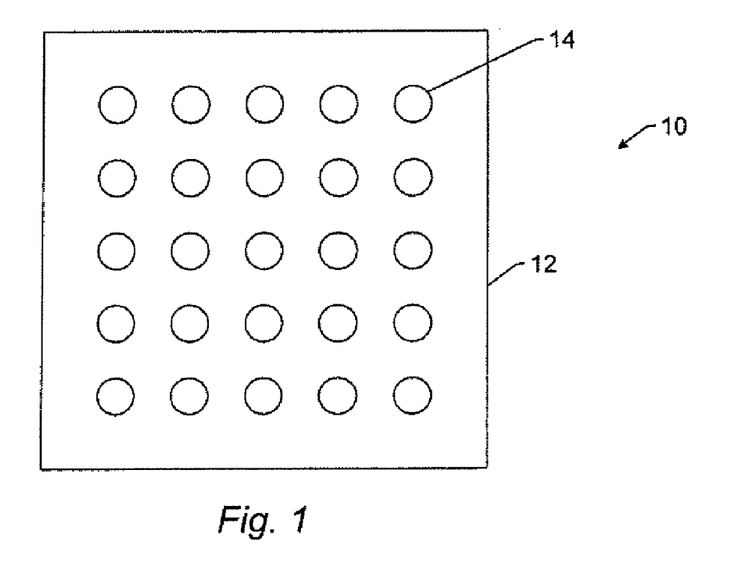
FIG. 1 is a schematic diagram illustrating a top view of one embodiment of a Fourier filter configured for use in an inspection system.

FIG. 1 illustrates one embodiment of a Fourier filter configured for use in an inspection system. In this embodiment, Fourier filter 10 includes substrate 12 that is substantially transparent to light (not shown in FIG. 1) from a specimen (not shown in FIG. 1) illuminated by the inspection system (not shown in FIG. 1). Fourier filter 10 also includes an array of patterned features 14 formed on substrate 12. The patterned features are formed of one or more pigments on the substrate. The patterned features are configured to block light reflected and diffracted from structures on the specimen and to allow light scattered from defects on the specimen to pass through the substrate. Therefore, the Fourier filter embodiments described herein are advantageously configured for use in an inspection system configured to detect defects based upon scattered light. For example, in one embodiment, the inspection system in which the Fourier filter is configured for use is configured as a dark field (DF) inspection system.

In some embodiments, as shown in FIG. 1, the array of patterned features includes a two-dimensional (2D) array of the patterned features. Therefore, the Fourier filter shown in FIG. 1 may be advantageously used to perform 2D Fourier filtering of the light from the specimen. Since diffraction peaks for flood based illumination systems are typically a 2D array of "dots," such a Fourier filter may be advantageously used in a flood illumination based inspection system. For example, in one embodiment, an area of the specimen illuminated by the inspection system, in which the Fourier filter is configured for use, includes a 2D field of view (FOV) on the specimen thereby "flood" illuminating the specimen. However, the array of patterned features may alternatively include a one-dimensional (1D) array of patterned features.

Although the array of patterned features of FIG. 1 is shown to include a particular number of patterned features, it is to be understood that an array of the patterned features included in the Fourier filter embodiments described herein may include any suitable number of patterned features positioned in any suitable arrangement on the substrate. In addition, although the patterned features are shown in FIG. 1 as having a generally circular shape, it is to be understood that the shape and dimensions of the patterned features may be selected as described further herein. In particular, the number, position, arrangement, shape, and any other characteristics of the patterned features may be selected based on an image of light at a Fourier plane of the system produced by a specimen to be inspected using the Fourier filter as described further herein. The array shown in FIG. 1 may be further configured as described herein.

Figure 5:
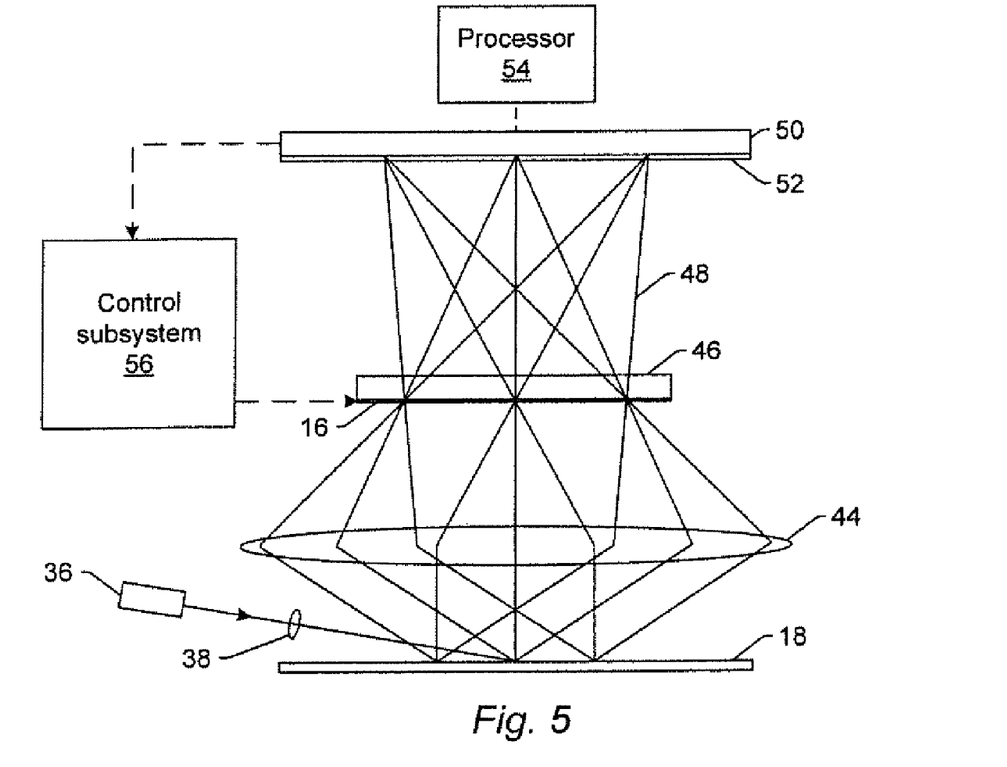
FIG. 5 is a schematic diagram illustrating a side view of one embodiment of a system configured to inspect a specimen.

The Fourier filter may be positioned at Fourier plane 16 of the system shown in FIG. 5, which is configured to inspect specimen 18. In particular, the Fourier filter may be positioned at a Fourier plane of a collection subsystem of the inspection system. The system shown in FIG. 5 may be further configured as described herein.

Figure 2:
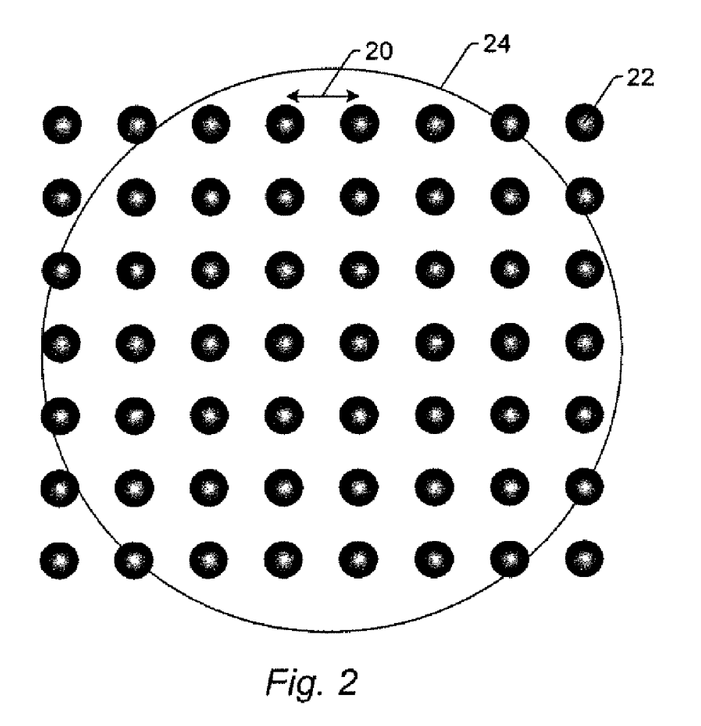
FIG. 2 is a schematic diagram illustrating a top view of one example of a diffraction pattern that may be observed in a Fourier plane of a flood illumination inspection system.

In one embodiment, the patterned features have a length of about 0.1 mm to about 2 mm and a width of about 0.1 mm to about 2 mm. In this manner, the patterned features may have an area of about 0.1 mm by about 0.1 mm to about 2 mm by about 2 mm. For example, for some technology nodes, the largest pitch of periodic structures that will be inspected may be fabricated using a 90 nm SRAM process with a unit cell size of about 1 µm by about 3 µm. The diffraction pattern produced by periodic structures having a 3 µm pitch at the Fourier plane of a system having a numerical aperture (NA) of about 0.7 is shown in FIG. 2, wherein the ANA spacing 20 between diffraction blurs 22 in Fourier plane 24 is $\lambda/\Lambda = 0.266$ µm/3 µm = 0.089, where $\lambda$ is wavelength and $\Lambda$ is pitch. For a system having a relatively high NA (e.g., an NA of about 0.9) and a Fourier plane having dimensions of about 20 mm, the distances between the diffraction orders will be about 1.9 mm.

For a maximum of about 16% blockage, the maximum Fourier plane blur allowed is about 0.86 mm in diameter. (16% blockage is used in this example merely as a frame of reference since it is the blockage of some currently used Fourier filters, which is preferably not exceeded by the embodiments of the Fourier filters described herein (e.g., since excess blockage may reduce the maximum defect signal detected by the system thereby reducing the defect sensitivity of the inspection system). In other words, good Fourier filtering performance is preferably achieved by blocking substantially all diffraction orders while blocking as little other scattered light as possible.) The allowable blur may vary depending on the optics of the inspection system (e.g., diffraction from the optics or the point spread function (PSF) of the optics).

In some embodiments, the specimen is illuminated by the inspection system with coherent illumination. For coherent illumination systems, the diffraction blur is on the order of about 0.15 mm. As such, the patterned features formed on the substrate may have a size of not less than about 0.15 mm. The Fourier filter "pixel" size or spot size of the one or more pigments may be less than about 50 µm, and placement (e.g., placement of the pixels on the substrate) is preferably better than about 25 µm. In some embodiments, therefore, each of the patterned features is formed of multiple spots of the one or more pigments such that the patterned features may provide substantially complete blockage of the diffraction. For example, an array of about 4 pixels by about 4 pixels, each pixel having a size of about 50 µm, may block a diffraction order with a diffraction blur of about 0.15 mm. In this manner, if the spots of the one or more pigments formed on the substrate have a size of about 50 µm, a 4×4 array of the one or more pigment spots may be used to print a single patterned feature on the substrate.

The area of the patterned features on the substrate is preferably selected such that substantially all of the diffraction is blocked by the patterned features with the smallest possible area. In addition, the size of the patterned features may be selected based on the diffraction blur in combination with the diffraction of the optics. For example, if the diffraction blur that is to be blocked by the Fourier filter has a size of about 1 mm, then the size of the patterned features may be about 1.3 mm to ensure that diffraction caused by the periodic structures on the specimen as well as any diffraction caused by the optics of the inspection system is blocked by the Fourier filter. In other embodiments, the specimen is illuminated by the inspection system with incoherent illumination. With incoherent illumination, an array of up to about 22 pixels by about 22 pixels, each pixel having a size of about 50 µm, may block the diffraction order.

Some specimens may include a number of different periodic structures formed thereon. For example, some specimens may include different regions, each or some of which include different periodic structures (e.g., periodic structures that have different pitches). In such instances, although it may be advantageous to use different Fourier filters for inspection of different periodic structures, each of which is optimized for the different periodic structures, changing the Fourier filter between different scans of the same specimen disadvantageously increases the time in which the inspection can be completed. However, different diffraction patterns produced by different periodic structures on the same specimen may be measured as described further herein, and a single Fourier filter may be fabricated that filters light reflected and diffracted from all of the different periodic structures. For example, the configuration of the patterned features of the Fourier filter may be selected such that the patterned features block light reflected and diffracted from different periodic structures. Such a Fourier filter may reduce the amount of scattered light, from each of the regions on the specimen in which different periodic structures are formed, which is allowed to pass through the Fourier filter. However, the amount of scattered light blocked by the Fourier filter may not be large enough to substantially reduce the sensitivity of the inspection system. Therefore, in some embodiments, the light blocked by the patterned features includes light reflected and diffracted from structures on the specimen having different diffraction patterns.

Figure 3:
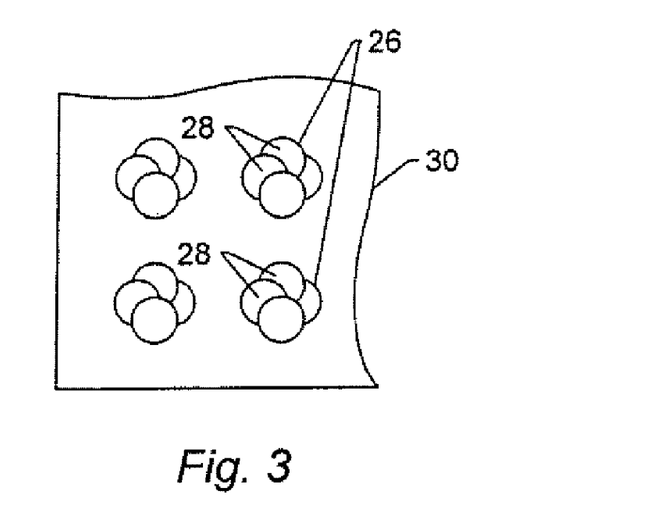
FIG. 3 is a schematic diagram illustrating a top view of one embodiment of patterned features of a Fourier filter that include multiple spots of one or more pigments.

One embodiment in which each of the patterned features of the Fourier filter is formed of multiple spots of one or more pigments is shown in FIG. 3. For example, as shown in FIG. 3, each of patterned features 26 may include four spots 28 of one or more pigments formed on substrate 30. Although each of the patterned features is shown in FIG. 3 as formed of four spots of one or more pigments, it is to be understood that each of the patterned features may be formed of any appropriate number of spots of the one or more pigments, which may be selected as described above. In addition, as shown in FIG. 3, spots 28 of each of patterned features 26 are formed such that the spots at least partially overlap one another. However, the spots of the patterned features may be formed such that each of the spots are formed adjacent to one another on the substrate without overlap between the spots.

In some embodiments, the patterned features have rough edges. For example, as further shown in FIG. 3, overlap of spots 28, which form each of patterned features 26, causes the patterned features to have relatively rough edges. In other words, the edges of the patterned features do not have a substantially circular shape. In particular, although the average shape of the edges of the patterned features may be generally circular, the edge actually has a relatively irregular shape that causes the edges to be relatively rough. In addition, or alternatively, the individual spots of one or more pigments that are used to form the patterned features may be formed with relatively rough edges. Therefore, even if the spots of the one or more pigments are printed such that the edges of the printed features have a generally regular shape, the spots themselves may impart roughness to the edges of the patterned features. In any case, the roughness of the edges of the patterned features may reduce the sharpness of the transitions between blocking and transmitting regions in the Fourier filter, which as described further herein is advantageous for reducing ringing in the output generated by the inspection system.

In another embodiment, the patterned features include apodized patterned features. For instance, the patterned features on the substrate may be formed in an additive process in which spots of one or more pigments may be formed on top of one another or overlapping as described above. In addition, individual spots of the one or more pigments may be relatively thin and may transmit some light such as deep ultraviolet (DUV) light. Therefore, the patterned features may be formed such that the thickness of the one or more pigments varies across the patterned features. For example, the thickness of the one or more pigments may be reduced near the edges of the patterned features to thereby form apodized patterned features. In particular, since the process for forming the patterned features is additive, many layers of different thicknesses may be used to form a single patterned feature that has a gradient in the thickness of the patterned feature and thereby a gradient from complete blockage to complete transmission.

Apodizing the patterned features in this manner may remove or smooth an otherwise relatively sharp transition in the transmission of the Fourier filter near the edges of the patterned features thereby effectively smoothing the transition between the light blocking patterned features and the light transmitting substrate, which advantageously reduces ringing in the output of the inspection system. In particular, smoothing the transition of the Fourier filter from blocking to transmitting as described above reduces the amount of the light that is diffracted into undesirable directions by the Fourier filter, which is commonly referred to as ringing or side lobes, and which reduces the imaging quality. In this manner, apodization of the patterned features may be used to control the transmission of the blocking features such that the sharpness of the edge is reduced thereby reducing the diffraction from the patterned features and the noise from ringing. As such, the apodization of the patterned features as described herein reduces the peripheral energy leakage in output generated during inspection of periodic structures, which would otherwise reduce defect sensitivities in the regions of the specimen containing the periodic structures. In some embodiments, therefore, the patterned features are configured such that the Fourier filter does not cause degradation of the output generated by the inspection system. In particular, the Fourier filter will not produce significant distortion at the image plane and thus will not adversely affect the ability of the inspection system to detect defects on the wafer with relatively high accuracy. Substrate 30 may be configured as described further herein.

In one embodiment, the substrate is formed of a substantially transparent material. In one such embodiment, the substantially transparent material includes fused silica, calcium fluoride ($CaF_2$), or magnesium fluoride ($MgF_2$). In another embodiment, the light from the specimen includes DUV light. For example, the Fourier filter may be printed on DUV grade fused silica using inkjet printing technology as described further herein. Such a substrate can meet the optical requirements of surface roughness and surface error for the Fourier filter.

In another embodiment, the Fourier filter includes one or more anti-reflection coatings formed on both sides of the substrate. In an additional embodiment, the Fourier filter includes one or more anti-reflection coatings formed on the substrate under the array of the patterned features. In this manner, the substrate of the Fourier filter may be coated with one or more anti-reflection (AR) coatings on both sides of the substrate. The AR coating(s) may be used to reduce "flare" and "ghosting," which are detrimental to coherent DF wafer inspection. Another use of the AR coating(s) is to modify the substrate surface, which the one or more pigments (e.g., the ink) would be formed on, such that the one or more pigments form relatively "tight" drops on the surface of the substrate instead of wetting the surface. In this manner, the AR coating (s) may be used to increase the controllability and predictability with which the patterned features can be formed on the substrate. The AR coating(s) may be formed on the substrate surface(s) in any suitable manner. In addition, the AR coating (s) may include any suitable AR coating(s) known in the art.

In some embodiments, the one or more pigments include ink printed on the substrate. For example, the ink may be printed on the substrate using an inkjet print head. Inkjet print heads with about 50 μm drop size (e.g., greater than about 510 dpi) are widely and commercially available. Placement of such print heads is better than about 25 μm, and accuracy is better than about 5 μm. (The placement generally depends on the accuracy with which the print head prints ink spots on the substrate when accurately positioned above the substrate, while the accuracy generally depends on the accuracy of the stage configured to position the print head over the substrate.) The turn around time for fabricating an inkjet printed Fourier filter is within a few minutes. The cost of ownership is relatively low since the consumables include ink and substrates. These characteristics make the inkjet approach attractive.

In some embodiments, the one or more pigments include one or more pigments that are curable by ultraviolet (UV) light. In another embodiment, the one or more pigments exhibit substantially no outgassing after being cured by light. In an additional embodiment, the one or more pigments exhibit substantially no outgassing without being cured by light. In a further embodiment, the one or more pigments exhibit substantially no outgassing when illuminated by the light from the specimen. In this manner, the one or more pigments may exhibit substantially low outgassing with and without light. For example, because the Fourier filter embodiments described herein may be used to filter light that includes DUV light, outgassing and photocontamination may occur if the one or more pigments are not chosen correctly. One of the most promising pigments for use in the embodiments described herein is UV curable ink. In particular, such an ink does not include solvents or volatile organic compounds (VOCs) after cure. In addition, such inks are relatively clean in that the nozzle of a print head used to print the patterned features on the substrate will not become clogged during printing. Furthermore, non-contact printing makes clearing a filter of the print head unnecessary. Therefore, using such ink to fabricate the Fourier filter embodiments described herein provides a tremendous saving in time and resources compared to using a lithography process to fabricate the Fourier filters.

In some embodiments, the Fourier filter includes an additional array of patterned features formed on the substrate. In one such embodiment, the patterned features of the additional array are configured to block light reflected and diffracted from structures on a different specimen and to allow light scattered from defects on the different specimen to pass through the substrate. Therefore, a single substrate may have different arrays of patterned features formed thereon thereby forming a Fourier filter that is capable of performing different Fourier filtering. As such, depending on the specimen being inspected by the inspection system, the position of the single substrate within the inspection system may be altered as described further herein such that the array of patterned features that can perform Fourier filtering for the specimen is positioned in the optical path of the inspection system.

Figure 4:
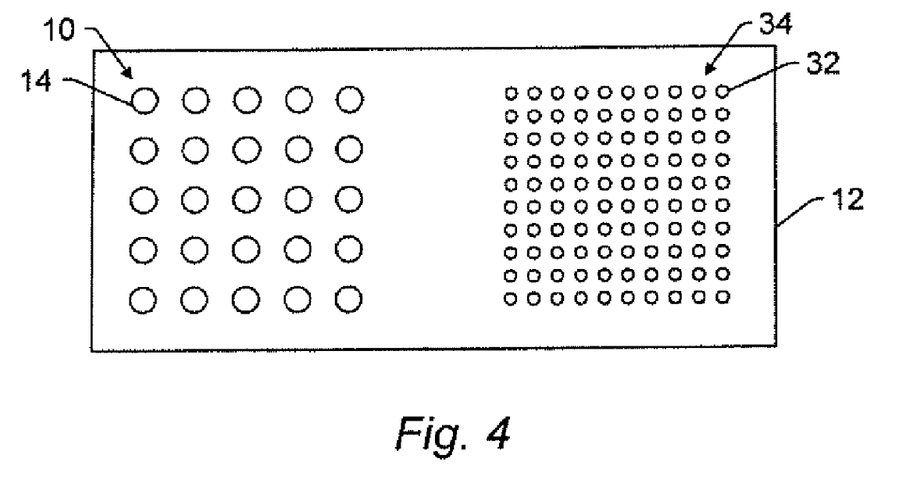
FIG. 4 is a schematic diagram illustrating a top view of one embodiment of a Fourier filter that includes two arrays of patterned features formed on a substrate, which are configured to block light reflected and diffracted from structures formed on different specimens and to allow light scattered from defects on the different specimens to pass through the substrate.

One example of such a Fourier filter is shown in FIG. 4. As shown in FIG. 4, substrate 12 includes array of patterned features 14. The array of patterned features 14 and the portion of substrate 12 on which patterned features 14 are formed thereby form Fourier filter 10. Fourier filter 10, substrate 12, and the array of patterned features 14 may be further configured as described herein. In addition, as shown in FIG. 4, array of patterned features 32 is also formed on substrate 12. Patterned features 14 and 32 have one or more different characteristics. For example, the patterned features of the different arrays may have different sizes and/or different pitches. The characteristics of the patterned features in both arrays may be selected as described further herein (e.g., based at least in part on the diffraction pattern that will be produced by a specimen when illuminated by the inspection system). The array of patterned features 32 may be further configured as described herein. The array of patterned features 32 and the portion of substrate 12 on which these patterned features are formed thereby form Fourier filter 34. As such, a single substrate may be used to form a Fourier filter capable of performing different Fourier filtering for different specimens.

In addition, as shown in FIG. 4, the different arrays of patterned features may be spaced from each other across the substrate. Such spacing of the different arrays of patterned features may be selected such that only one of the different arrays may be positioned in the optical path of the inspection system at a time, preferably while reducing the amount by which the substrate is translated in order to change the array of patterned features that is positioned in the optical path of the inspection system. Furthermore, although two different arrays of patterned features are shown formed on substrate 12 in FIG. 4, it is to be understood that any suitable number of arrays of patterned features may be formed on substrate 12 and arranged on substrate 12 in any suitable manner. For instance, the arrays of patterned features may be formed on the substrate such that they are spaced across one dimension of the substrate (e.g., in a 1D array) or across two dimensions of the substrate (e.g., in a 2D array), The embodiments described herein, therefore, provide a mask (e.g., a printable mask) that can be used for spatial Fourier filtering in flood illuminated DF inspection systems. Fourier filtering is commonly used in DF inspection systems to filter out a repetitive pattern. Defect signals in the array areas will be enhanced tremendously in such a system due to such filtering. However, during use, the filter will be positioned in the high resolution imaging path of the inspection system with relatively high NA (e.g., an NA of about 0.5 to about 0.99) and relatively short wavelengths (e.g., less than about 300 nm). Relatively stringent surface error requirements for the Fourier filter may include a surface roughness of less than about 4 nm, less than about ¹⁄₄₀ wave higher order surface error (e.g., for 3rd orders and higher), and apodized filter patterns to reduce ringing in the final image. Because of variations in periodic structures of specimens that may be inspected with the same system, a relatively quick turn around time (e.g., on the order of about 10 minutes) is preferable for fabricating the Fourier filter embodiments in the production environment. In particular, since different Fourier filters are needed for inspection of specimens having different periodic structures formed thereon, fabrication of the Fourier filters is preferably relatively quick to minimize any delays in when the specimens can be inspected. In addition, although the design file for the Fourier filter may be sent out to a mask house or lithography may be performed in house or in fab, these processes are generally too cumbersome, too slow, and require considerable capital investment particularly in comparison to the fabrication processes described herein. The area of blockage of the Fourier filter is also preferably minimal while still blocking substantially all diffraction patterns and different modes of operation. The Fourier filter embodiments (e.g., the inkjet printed Fourier filter embodiments) described herein advantageously meet all of the above-described Fourier filter requirements without the major drawbacks of other currently used Fourier filters.

The Fourier filter embodiments described herein have, therefore, a number of advantages over other Fourier filters. For example, the Fourier filter embodiments described herein have relatively high optical quality, relatively small specimen distortion, and relatively small scattering. In addition, the Fourier filter embodiments described herein may be formed on a relatively high quality DUV transmitting substrate such as fused silica. As such, the Fourier filters do not have any pixilated artifices. Furthermore, as described further herein, the Fourier filter embodiments are also formed using a relatively high resolution and additive process that makes apodization and controlled rough edges of the patterned features possible, which can be used to minimize ringing created by the Fourier filters. The Fourier filter embodiments described herein also are compatible with semiconductor fabrication environments in that they are formed using one or more non-contaminating pigments and no cleaning is necessary. Moreover, the Fourier filter embodiments described herein may be produced in a relatively fast turn around time (e.g., within minutes). In addition, the Fourier filter embodiments described herein have a substantially low cost of ownership (e.g., just the cost of the one or more pigments (e.g., an ink) and the substrate).

FIG. 5 illustrates one embodiment of a system configured to inspect a specimen. The system includes an illumination subsystem configured to illuminate specimen 18. The illumination subsystem includes light source 36. Light source 36 may be any suitable light source known in the art such as a laser light source. The systems described herein may, therefore, be configured for narrow band (NB) illumination and inspection. The light source may be configured to generate light having any suitable wavelength or wavelengths known in the art such as visible, UV, DUV, near vacuum ultraviolet (near-VUV), VUV, or some combination thereof. For example, the light source may be configured to generate light having wavelength(s) of less than about 300 nm. The wavelength(s) of the light generated by the light source may be selected based on, for example, one or more characteristics of the specimen, one or more characteristics of the defects of interest, and one or more characteristics of other optical components of the system. In addition, the light source may be configured to generate coherent light or incoherent light. The illumination subsystem may also be configured to illuminate the specimen with coherent light or incoherent light.

The illumination subsystem may also include objective 38. Objective 38 may be configured to focus light generated by light source 36 onto specimen 18. In addition, as shown in FIG. 5, objective 38 is configured to direct the light to the specimen at an oblique angle of incidence. The oblique angle of incidence may include any suitable oblique angle of incidence known in the art. Objective 38 may include one refractive optical element as shown in FIG. 5. However, objective 38 may alternatively include one or more refractive optical elements and/or one or more reflective optical elements. In addition, objective 38 may include any suitable optical element(s) known in the art.

The illumination subsystem may also include any other suitable optical elements (not shown) known in the art. Examples of such optical elements include, but are not limited to, spectral filters, polarizing components, beam shaping elements, apertures, and any other optical elements known in the art.

The illumination subsystem described above is also configured to illuminate a 2D FOV on the specimen. For example, the illumination subsystem may be configured to illuminate an area on the specimen that includes a relatively large number of pixels in two opposing directions (e.g., one hundred or more pixels by one hundred or more pixels). Such an illumination subsystem provides a type of illumination that may be commonly referred to as "flood illumination." In contrast to flood illumination, spot illumination used in spot scanning inspection systems commonly illuminates relatively few pixels on the specimen.

Figure 6:
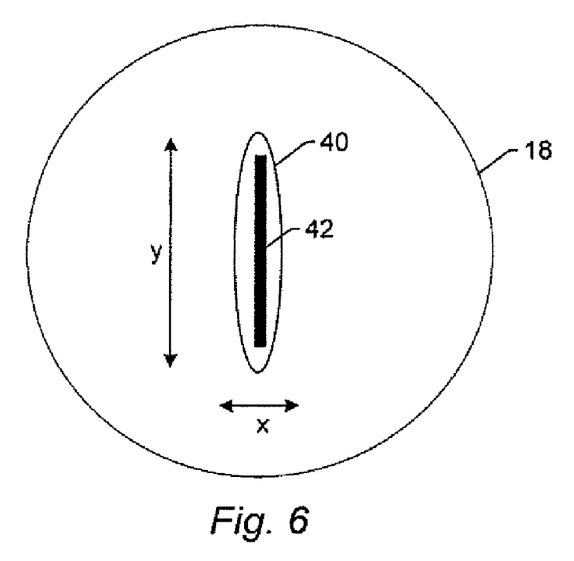
FIG. 6 is a schematic diagram illustrating a top view of one embodiment of a two-dimensional field of view (FOV) that may be illuminated on a specimen by a system embodiment described herein and a FOV of a detection subsystem of the inspection system.

In one embodiment, the FOV has an approximately elliptical (or "oblong") shape on the specimen. For example, as shown in FIG. 6, FOV 40 has an approximately elliptical shape on specimen 18. Such a shape of the FOV may be caused by the angle of incidence at which the illumination subsystem directs light to the specimen. For example, a light beam that has a substantially circular cross-section may appear to have a substantially elliptical cross-section when projected onto the specimen at an oblique angle of incidence. As further shown in FIG. 6, light scattered from FOV 40 on specimen 18 may be imaged onto FOV 42 of a detector (not shown in FIG. 6), which is shown in FIG. 6 superimposed on FOV 40 to illustrate the similarities in the shapes of the FOVs. For example, as shown in FIG. 6, the shapes of the FOVs are to relatively similar such that a substantial portion of the pixels in the illuminated FOV on the specimen can be imaged onto pixels in the FOV of the detector. In one embodiment, the detector may be a time delay integration (TDI) camera that has a 2D array of pixels. In one such embodiment, the TDI camera may include about 400 pixels along one dimension of the TDI camera and about 4000 pixels along the opposite dimension. The x and y directions shown in FIG. 6 are referenced to the specimen plane, and scanning of the FOV across the specimen may be performed in the x direction.

The system shown in FIG. 5 also includes a collection subsystem configured to collect light from specimen 18. In one embodiment, the collection subsystem includes lens 44 that is configured to collect light scattered from specimen 18. Lens 44 is also configured to collect light diffracted from periodic structures (not shown) on specimen 18. The periodic structures may include any periodic structures known in the art. Lens 44 may include an objective lens, a Fourier transform lens, or any other suitable optical element known in the art. In addition, although the collection subsystem is shown in FIG. 5 to include one lens, it is to be understood that the collection subsystem may include more than one optical element (one or more refractive optical elements and/or one or more reflective optical elements). Furthermore, the collection subsystem may include any other suitable optical element(s) (not shown) known in the art. The light from the specimen may include DUV light if the specimen is illuminated by the illumination subsystem in this wavelength range.

The system shown in FIG. 5 also includes Fourier filter 46 positioned at Fourier plane 16 of the collection subsystem. The Fourier filter may be configured as described herein. For example, Fourier filter 46 includes a substrate (such as that shown in FIG. 1) that is substantially transparent to the light from the specimen and an array of patterned features (such as that shown in FIG. 1) formed on the substrate. The substrate and the array of patterned features may be configured as described herein. For example, the patterned features are formed of one or more pigments on the substrate. In addition, the patterned features are configured to block light reflected and diffracted from structures on the specimen and to allow light scattered from defects on the specimen to pass through the substrate. The array of the patterned features of the Fourier filter may extend across substantially the entire optical path of the system (e.g., across substantially the entire Fourier plane).

As described further herein, the inspection system may be configured as a DF inspection system and a flood illumination based inspection system. Therefore, the Fourier filter may be used as a 2D Fourier filter in a flood illumination based DF inspection system. In particular, the array of patterned features may be configured as described further herein such that these patterned features block a 2D pattern of light diffracted from periodic structures on the specimen. The patterned features may, therefore, be arranged in a 2D array that is selected based on one or more characteristics (e.g., dimensions, pitch, etc.) of the periodic structures on the specimen. The 2D pattern fanned by the patterned features may, therefore, correspond to a 2D pattern formed in the Fourier plane by diffracted peaks of light collected by the collection subsystem. As such, the characteristics of the Fourier filter may be selected such that the 2D array substantially prevents a 2D pattern of light diffracted from periodic structures on the specimen from passing through the Fourier filter.

Blocking light diffracted from periodic structures on a specimen in the inspection systems described herein is advantageous for a number of reasons. For example, light diffracted from periodic structures on the specimen tends to be relatively bright in comparison to light scattered from defects on the specimen. Therefore, blocking light diffracted from the periodic structures on the specimen prevents the diffracted light from being detected (e.g., by a detection subsystem described further herein) thereby increasing the accuracy with which light scattered from defects can be detected. In addition, light diffracted from periodic structures tends to propagate in fairly predictable directions while light scattered from defects tends to scatter fairly randomly. Therefore, preventing light diffracted from the periodic structures on the specimen from being detected by blocking the diffracted light allows the light scattered from defects to be detected more easily.

Unlike some Fourier filters such as mechanical filters and previous implementations of Fourier filters, the embodiments of the Fourier filters described herein do not block light along an entire dimension of the Fourier filter. In other words, unlike previous Fourier filters that were only capable of or only used to block light one-dimensionally, the Fourier filter embodiments described herein are capable of and are used to block light two-dimensionally. In this manner, the Fourier filter embodiments described herein are configured such that the diffraction peaks in the light from the specimen can be blocked while allowing a larger amount of light to be detected. For example, the Fourier filter embodiments described herein can allow a larger amount of light scattered from defects on the specimen to pass through the Fourier filter compared to mechanical filters and previous implementations of Fourier filters. As such, the Fourier filter embodiments described herein can be used to provide a system that detects higher defect signals and therefore has higher defect detection sensitivity than other currently available systems. The embodiments of the Fourier filters described herein are also advantageous for a number of additional reasons set forth herein.

The system shown in FIG. 1 also includes a detection subsystem configured to generate output responsive to light 48 that passes through the substrate. The detection subsystem includes, in this embodiment, detector 50 positioned at image plane 52 of the system. The detection subsystem may also include an objective (not shown) configured to image light that passes through Fourier filter 46 onto detector 50. The objective may include, for example, any suitable imaging lens(es) or focusing lens(es) known in the art. Detector 50 may be any appropriate detector known in the art such as a charge coupled device (CCD) or TDI camera. Detector 50 may be configured to generate the output responsive to the light that passes through the substrate of the Fourier filter. The detection subsystem may also include any other suitable optical element(s) (not shown) known in the art.

The output generated by the detection subsystem can be used to detect defects (not shown) on the specimen. For example, the system may include processor 54. Processor 54 may be coupled to detector 50 of the detection subsystem by a transmission medium (not shown). The transmission medium may include any suitable transmission medium known in the art. In addition, the processor may be coupled to the detector by one or more electronic components (not shown) such as an analog-to-digital converter. In this manner, processor 54 is configured to receive output from detector 50.

Processor 54 may be configured to use the output to detect defects on the specimen. The defects may include any defects of interest on the specimen. In addition, the processor may be configured to use the output and any method and/or algorithm known in the art to detect the defects on the specimen. Furthermore, processor 54 may be configured to perform any other inspection-related functions known in the art (e.g., defect location determination, defect classification, defect mapping, etc.).

Processor 54 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

In one embodiment, the system shown in FIG. 5 includes control subsystem 56. Control subsystem 56 is configured to align the Fourier filter in the Fourier plane by translating the Fourier filter within the Fourier plane until an intensity measured by the detection subsystem is minimized. In this manner, the control subsystem can align the filter to overlap with diffraction orders produced by periodic structures on specimen 18 until a minimum intensity is imaged on the detector. For example, the control subsystem may be coupled to detector 50 of the detection subsystem. The control subsystem may be coupled to the detector as described above. The Fourier filter may be inserted into a holder (not shown) mounted on a stage (not shown) such as an x-y stage. The control subsystem may be coupled to the stage in any suitable manner. In addition, the control subsystem may be coupled to the stage and configured such that the control subsystem can alter a position of the Fourier filter by causing a position of the stage to change. For example, the control subsystem may include any suitable mechanical and/or robotic assembly that can be configured to move the stage and thereby alter the position of the filter. The control subsystem may also be configured to move the Fourier filter by causing the Fourier filter to be translated in the x and y directions within the Fourier plane. If the system includes a subsystem (not shown) for altering the focus of the system (e.g., to account for variations in the height of the specimen), the control subsystem may also be configured to move the Fourier filter in the z direction (e.g., toward and away from the specimen) such that the Fourier filter may be relatively accurately positioned in the Fourier plane of the collection subsystem.

In this manner, the Fourier filter may initially be positioned in the Fourier plane, and the detector may generate output responsive to the light that passes through the Fourier filter. The control subsystem may receive the output from the detector and determine the intensity of the light that passed through the Fourier filter across the FOV of the detection subsystem. The control subsystem may determine if and how the Fourier filter should be moved within the Fourier plane (and possibly in the z direction) based on the intensity of the light that passed through the Fourier filter. Output may again be generated by the detector after the control subsystem has caused the Fourier filter to be moved as determined above, and the control subsystem may use this additional output to determine the intensity of the light that passed through the Fourier filter across the FOV of the detection subsystem. These steps may be repeated until the Fourier filter is positioned such that a minimum intensity of the light across the FOV of the detection subsystem passes through the Fourier filter. The control subsystem may be configured to determine the intensity as described above, to determine if and how the Fourier filter should be moved as described above, and to identify the minimum intensity as described above using any suitable method and/or algorithm. Such positioning of the Fourier filter may be performed each time the Fourier filter in the optical path of the inspection system is changed.

If more than one array of patterned features is formed on a single substrate as described above, the control subsystem may also move the substrate as described above such that the appropriate array of patterned features is positioned in the optical path for inspection of different specimens. Furthermore, the control subsystem may be configured to alter the holder that is positioned on the stage to thereby change the Fourier filter that is positioned at the Fourier plane of the inspection system. Such alteration of the holder may be accomplished by the control subsystem in any manner known in the art.

As described above, the Fourier filter may be inserted into a holder (not shown) mounted on a stage (not shown) such as an x-y stage. Inserting the Fourier filter into a holder mounted on an x-y stage may increase the ease of filter alignment and filter selection. In addition, the filter may be positioned in the holder for easy "drop in" and to maintain tolerance for the Fourier filter. Furthermore, the holder may include a cassette configured such that different Fourier filters may be positioned in different slots in the cassette. Such a cassette may have any suitable configuration known in the art. In addition, a Fourier filter in the cassette may be positioned in the optical path of the inspection system by the control subsystem as described further herein.

It is noted that FIG. 5 is provided herein to generally illustrate one configuration of an embodiment of a system configured to inspect a specimen. Obviously, the system configurations described herein may be altered to optimize the performance of the system as is normally performed when designing a commercial inspection system. In addition, the systems described herein may be implemented using an existing inspection system (e.g., by inserting an embodiment of a Fourier filter described herein in an existing inspection system such as one of the Puma 9000 Series tools that are commercially available from KLA-Tencor, San Jose, Calif.). For some such systems, the inspection functionality described herein may be provided as optional functionality of the system (e.g., in addition to other functionality of the system). Alternatively, the systems described herein may be designed "from scratch" to provide a completely new system.

Figure 7:
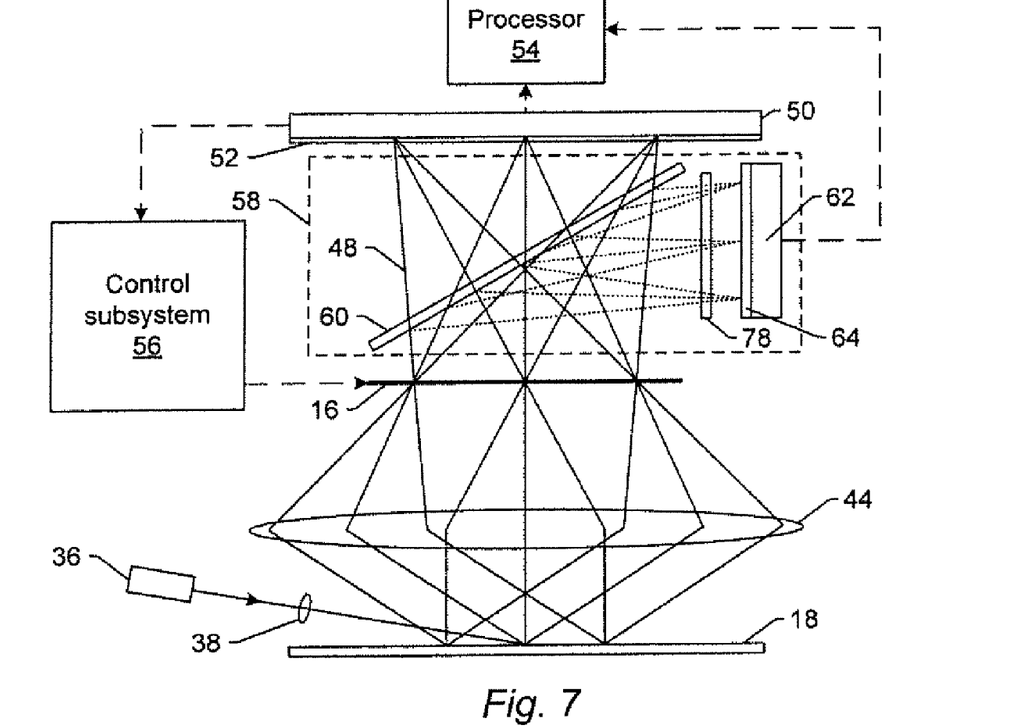
FIGS. 7-8 are schematic diagrams illustrating a side view of different portions of one embodiment of a system configured to fabricate a Fourier filter for use in an inspection system.
Figure 8:
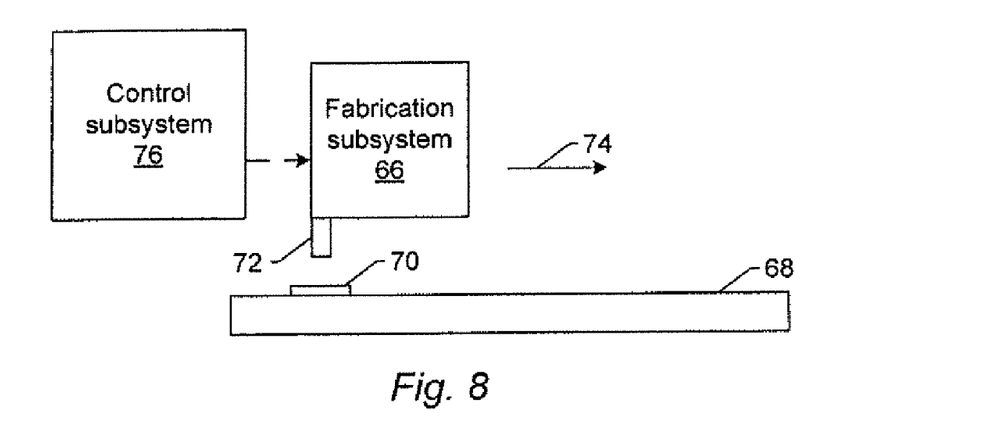

An additional embodiment relates to a system configured to fabricate a Fourier filter for use in an inspection system. Different portions of one embodiment of such a system are shown in FIGS. 7 and 8. A view of the Fourier plane can be used to measure the diffraction pattern that should be blocked by the Fourier filter that is to be fabricated. For example, as shown in FIG. 7, the system includes optical subsystem 58 that is configured to generate an image of light in Fourier plane 16 of the inspection system shown in FIG. 5. The light is reflected and diffracted from structures on a specimen. In particular, in this embodiment, unlike the inspection system shown in FIG. 5, a Fourier filter is not positioned at Fourier plane 16 such that the optical subsystem may measure light reflected and diffracted from periodic structures of the specimen.

As shown in FIG. 7, the optical subsystem may include beam splitter 60. Beam splitter 60 may include any suitable optical component known in the art. For instance, beam splitter 60 may include a partially transmissive mirror. However, another optical component such as a minor (not shown) may be used instead of beam splitter 60 to view the Fourier plane. Beam splitter 60 or another suitable optical component may be positioned in the path of the light that passes through Fourier plane 16 of the system only when the image of the light in the Fourier plane of the inspection system is being measured for fabrication of a new Fourier filter. For instance, during inspection of a specimen for which a Fourier filter has been fabricated, the beam splitter or other optical component may be removed from the optical path of the inspection system. The beam splitter or other optical component may be removed from the optical path of the inspection system in any manner known in the art. For example, the optical component may include a flip-in mirror (not shown), and the position of the flip-in minor may be controlled by control subsystem 56 or processor 54. In another example, the control subsystem may alter a position of the beam splitter much in the same way as described above with respect to control of the position of the Fourier filter in the optical path.

As further shown in FIG. 7, the optical subsystem includes detector 62 positioned at image plane 64. Detector 62 may include any of the detectors described herein and may include any other suitable viewer or camera known in the art. Detector 62 is configured to generate output responsive to an image of the light in the Fourier plane of the system, including light reflected and diffracted from the structures (e.g., periodic structures) on the specimen. As shown in FIG. 7, detector 62 may be coupled to processor 54 such that the processor may receive the image from the detector. The processor may be coupled to detector 62 as described further herein. The optical subsystem may also include any other suitable optical components (not shown). For example, the optical subsystem may include a lens positioned between the beam splitter and detector 62. The lens may be configured to image the Fourier plane onto image plane 64.

The system configured to fabricate the Fourier filter also includes fabrication subsystem 66 shown in FIG. 8 that is configured to form an array of patterned features (not shown) on substrate 68 with one or more pigments 70 to thereby fabricate the Fourier filter. In addition, the fabrication subsystem may include nozzle 72 through which the fabrication subsystem dispenses the one or more pigments onto the substrate. The nozzle may have any suitable configuration known in the art, and the nozzle configuration may affect the drop size of the one or more pigments on the substrate. Therefore, fabrication subsystems that have different nozzle configurations may be selected for use for fabricating the Fourier filter based on the selected drop size.

In some embodiments, the fabrication subsystem includes a print head configured to form the array of the patterned features on the substrate. The print head may include any suitable print head known in the art. For example, the print head may include an inkjet print head, and many commercially available inkjet print heads may be suitable for use in the embodiments described herein. Therefore, a Fourier filter described herein can be fabricated using an inkjet print head. In addition, the fabrication subsystem may be configured to form one or more patterned features on the substrate sequentially by scanning across the substrate in a direction such as that shown by arrow 74. Substrate 68 is substantially transparent to light from the specimen. Substrate 68 may be further configured as described herein.

In one embodiment, the fabrication subsystem is configured to form drops of the one or more pigments having a size of greater than about 500 dpi. In another embodiment, the one or more pigments include one or more pigments that are curable by UV light. In one such embodiment, the system shown in FIGS. 7 and 8 may include a curing subsystem (not shown) that may include at least a light source configured to generate UV light or other appropriate light. The curing subsystem may also be configured to direct the UV light to a substrate on which the patterned features have been formed using one or more pigments that may include a UV curable ink. One or more parameters (e.g., wavelength(s), duration, etc.) of the process for curing the one or more pigments may vary depending on the pigments themselves. In this manner, if different Fourier filters are to be printed with different pigments and/or if multiple pigments are to be used to fabricate a single Fourier filter, one or more parameters of the curing process may be altered and controlled by the system (e.g., by control subsystem 72). In addition, to prevent contamination of the inspection system or any other systems in the same environment as the curing subsystem, the curing process may be performed in a properly ventilated housing (not shown), which may be included in the system and may include any appropriate ventilated housing known in the art. Another advantage of using one or more UV curable pigments is that the pigments are relatively clean in that they will not clog nozzle 72 of fabrication subsystem 66.

The system shown in FIGS. 7 and 8 also includes control subsystem 76 configured to control fabrication subsystem 66 based on the image generated by optical subsystem 58 such that the patterned features formed on substrate 68 block the light reflected and diffracted from the structures (e.g., periodic structures) on the specimen and allow light scattered from defects on the specimen to pass through the substrate. Control subsystem 76 may be configured to receive the image generated by optical subsystem 58 from processor 54, if processor 54 is configured to receive the image as described above. For example, control subsystem 76 may be coupled to processor 54 as described herein. Alternatively, control subsystem 76 may be configured to receive the image generated by the optical subsystem from the optical subsystem (e.g., from detector 62 of the optical subsystem). For example, control subsystem 76 may be coupled to detector 62 as described herein such that the control subsystem may receive the image generated by the detector. In addition, although the system shown in FIGS. 7 and 8 includes control subsystem 56 for positioning the Fourier filter in the Fourier plane and control subsystem 76 for controlling the fabrication subsystem, it is to be understood that this system may include a single control subsystem that is configured to both position the Fourier filter in the Fourier plane and to control the fabrication subsystem.

Control subsystem 76 may be configured to control the fabrication subsystem in any suitable manner. For example, the control subsystem may be configured to generate a write file or a recipe for forming the patterned features on the substrate. The write file may be created by using the diffraction pattern in the image generated by the optical subsystem and pattern recognition to identify the diffraction pattern and the different diffraction orders in the image. The control subsystem may then determine the position and other characteristics (e.g., size, shape, etc.) of the patterned features to be formed on the substrate by the fabrication subsystem based on the diffraction pattern and the different diffraction orders (possibly in combination with other information described herein). The control subsystem may then use the write file or recipe to control the fabrication subsystem or may provide the write file or the recipe to the fabrication subsystem such that the fabrication subsystem may form the patterned features on the substrate.

If more than one array of patterned features are formed on a single substrate, the control subsystems described herein may use the write files to determine which arrays of patterned features are formed in different regions of the substrate and to thereby position the appropriate array of patterned features in the optical path of the inspection system during inspection of different specimens. In addition, the control subsystem may be configured to determine fiducial marks or some indicia that can be used to identify the Fourier filters in different holders or at different positions on a single substrate. Such fiducial marks may include any suitable indicia and may also include one or more features that can be used to perform rough or coarse alignment of the Fourier filter in the optical path of the inspection system. The inspection system may also include a separate viewing system (not shown) for "reading" fiducial marks or other indicia printed on the substrate of the Fourier filter. The fiducial marks may also be "read" to determine if the correct Fourier filter has been positioned in the optical path of the inspection system (e.g., the fiducial mark(s) of the correct Fourier filter may be included in an inspection recipe for a particular specimen and compared to the fiducial mark(s) read on the Fourier filter positioned in the optical path of the inspection system prior to inspection). Such fiducial marks may be included in the write file or recipe used to fabricate the Fourier filter and may be formed on the substrate in the same process in which the patterned features are formed on the substrate.

In some embodiments, the system shown in FIGS. 7 and 8 includes mask 78 having known features (not shown) formed thereon. The mask may have any suitable configuration known in the art. In one such embodiment, control subsystem 76 is configured to calibrate the optical subsystem prior to imaging of the light in the Fourier plane. For example, the mask of known features may be positioned in the optical path from the beam splitter to detector 62 as shown in FIG. 7 or in the Fourier plane, and the light transmitted through the mask and imaged onto image plane 64 may be imaged by the detector. The control subsystem may use this image to calibrate the magnification and/or distortion of the optical subsystem. For example, because the magnification of the optical subsystem may be different than that of the inspection system, the control subsystem may be configured to calibrate the magnification of the optical subsystem. The calibration may be performed such that based on the image produced using the mask, the 2D FOV of detector 62 can be matched to the 2D FOV of lens 44. In this manner, detector 62 may generate an image of the Fourier plane such that when designing a Fourier filter, a specimen may be positioned in the inspection system and the diffraction pattern may be recorded with alterations made for adjusting the magnification of the optical subsystem.

In one embodiment, the light in the Fourier plane imaged by the optical subsystem includes light reflected and diffracted from all structures formed on the specimen. For example, a scan through all of the periodic structures on the specimen may be performed to capture all of the diffraction patterns that will be produced by the periodic structures (e.g., since different periodic structures may produce different diffraction patterns). The optical subsystem may be configured to image the light reflected and diffracted from all structures formed on the specimen by scanning the optical subsystem over the specimen and thereby over different regions of the specimen containing different periodic structures, and such scanning may be performed in any suitable manner known in the art. In one such embodiment, control subsystem 76 is configured to control fabrication subsystem 66 based on the image generated by the optical subsystem, diffraction orders of interest, a calibration factor, and tolerances and diffraction width. For example, a Fourier filter design optimized for a particular specimen can be produced using a superposition of all diffraction patterns, one or more thresholds for the diffraction orders of interest, the applied calibration factor, and added tolerances for the diffraction width.

The Fourier filter may be designed based on the superposition of all diffraction patterns produced by a specimen since different areas on the specimen may produce different diffraction patterns. Ideally, the Fourier filter would be changed for inspection of the different areas. However, the throughput of inspection systems is generally too high to make such changing of the Fourier filter feasible in a single scan of the specimen. As such, the entire specimen may be scanned to determine the configuration for a single Fourier filter that can be used for inspection of the entire specimen. In addition, the superposition of all diffraction patterns that will be produced by all periodic structures on a specimen may be determined in addition to a superposition of the diffraction patterns that will be produced by periodic structures in only the "care areas" on the specimen (i.e., the areas on the specimen that the user "cares" about). The different superpositions may be generated based on output acquired by the optical subsystem in a single scan (by segmenting the output based on area on the specimen for which the output was generated) or in multiple scans (one scan of the entire specimen and at least one scan of only selected areas on the specimen). More than one Fourier filter may then be fabricated based on the different superpositions and used for different inspections of the specimen (e.g., an inspection of the entire specimen and an inspection of only the care areas on the specimen). In addition, the configuration of a single Fourier filter may be determined based on the different superpositions such that the single Fourier filter is configured for better Fourier filtering in the care areas of the specimen than the non-care areas of the wafer.

The one or more thresholds for the diffraction orders of interest may be used to differentiate between the diffraction in the Fourier plane and noise in the image of the Fourier plane produced by the optical subsystem (e.g., by detector 62) and/or defects on the specimen. In this manner, the one or more thresholds may be used to reduce the difficulty of designing and fabricating the Fourier filter and may reduce the blockage of the Fourier filter, which may be increased if the Fourier filter is designed to block noise in the image from the detector or the defects. The added tolerances for the diffraction width may include mechanical tolerances for placing the filter in the inspection system and mechanical tolerances of fabricating the filter.

In some embodiments, the control subsystem is configured to control the fabrication subsystem to cause the patterned features to have apodization. The apodization may be configured as described further herein and may be caused as described further herein. In addition, the appropriate apodization for the patterned features may be determined using any suitable algorithm and/or method known in the art. In another embodiment, the control subsystem is configured to control the fabrication subsystem to cause the patterned features to have rough edges. The rough edges of the patterned features may be configured as described herein and may be formed as described further herein. The roughness of the edges for the patterned features may be determined using any suitable algorithm and/or method known in the art. In one such embodiment, apodization and rough edges for the patterned features may be included in the write files or recipes for fabrication of the Fourier filters to reduce the ringing effect as described further herein.

Further modifications and alternative embodiments of various aspects of the invention may be apparent to those skilled in the art in view of this description. For example, Fourier filters, inspection systems, and systems for fabricating Fourier filters are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A Fourier filter configured for use in an inspection system, comprising:
   a substrate that is substantially transparent to light from a specimen illuminated by the inspection system; and
   an array of patterned features formed on the substrate, wherein the patterned features are formed of one or more pigments on the substrate, wherein the patterned features are configured to block light reflected and diffracted from structures on the specimen and to allow light scattered from defects on the specimen to pass through the substrate, and wherein the one or more pigments exhibit substantially no outgassing when illuminated by the light from the specimen.

2. The Fourier filter of claim 1, wherein the one or more pigments comprise ink printed on the substrate.

3. The Fourier filter of claim 1, wherein an area of the specimen illuminated by the inspection system comprises a two-dimensional field of view on the specimen.

4. The Fourier filter of claim 1, wherein the light from the specimen comprises deep ultraviolet light.

5. The Fourier filter of claim 1, wherein the inspection system is configured as a dark field inspection system.

6. The Fourier filter of claim 1, wherein the specimen is illuminated by the inspection system with coherent illumination.

7. The Fourier filter of claim 1, wherein the specimen is illuminated by the inspection system with incoherent illumination.

8. The Fourier filter of claim 1, wherein the array of patterned features comprises a two-dimensional array of the patterned features.

9. The Fourier filter of claim 1, wherein the patterned features comprise apodized patterned features.

10. The Fourier filter of claim 1, wherein the patterned features have rough edges.

11. The Fourier filter of claim 1, wherein the patterned features have a length of about 0.1 mm to about 2 mm and a width of about 0.1 mm to about 2 mm.

12. The Fourier filter of claim 1, wherein each of the patterned features is formed of multiple spots of the one or more pigments.

13. The Fourier filter of claim 1, wherein the light blocked by the patterned features comprises light reflected and diffracted from structures on the specimen having different diffraction patterns.

14. The Fourier filter of claim 1, further comprising an additional array of patterned features formed on the substrate, wherein the patterned features of the additional array are configured to block light reflected and diffracted from structures on a different specimen and to allow light scattered from defects on the different specimen to pass through the substrate.

15. The Fourier filter of claim 1, wherein the substrate is formed of a substantially transparent material, and wherein the substantially transparent material comprises fused silica, calcium fluoride, or magnesium fluoride.

16. The Fourier filter of claim 1, further comprising one or more anti-reflection coatings formed on both sides of the substrate.

17. The Fourier filter of claim 1, further comprising one or more anti-reflection coatings formed on the substrate under the array of the patterned features.

18. The Fourier filter of claim 1, wherein the one or more pigments comprise one or more pigments that are curable by ultraviolet light.

19. The Fourier filter of claim 1, wherein the one or more pigments exhibit substantially no outgassing after being cured by light.

20. The Fourier filter of claim 1, wherein the one or more pigments exhibit substantially no outgassing without being cured by light.

21. A system configured to inspect a specimen, comprising:
   an illumination subsystem configured to illuminate a two-dimensional field of view on the specimen;
   a collection subsystem configured to collect light from the specimen;
   a Fourier filter positioned at a Fourier plane of the collection subsystem, wherein the Fourier filter comprises a substrate that is substantially transparent to the light from the specimen and an array of patterned features formed on the substrate, wherein the patterned features are formed of one or more pigments on the substrate, wherein the patterned features are configured to block light reflected and diffracted from structures on the specimen and to allow light scattered from defects on the specimen to pass through the substrate, and wherein the one or more pigments exhibit substantially no outgassing when illuminated by the light from the specimen; and
   a detection subsystem configured to generate output responsive to the light that passes through the substrate, wherein the output is used to detect the defects on the specimen.

22. The system of claim 21, further comprising a control subsystem configured to align the Fourier filter in the Fourier plane by translating the Fourier filter within the Fourier plane until an intensity measured by the detection subsystem is minimized.

23. A system configured to fabricate a Fourier filter for use in an inspection system, comprising:
   an optical subsystem configured to generate an image of light in a Fourier plane of the inspection system, wherein the light is reflected and diffracted from structures on a specimen;
   a fabrication subsystem configured to form an array of patterned features on a substrate with one or more pigments to thereby fabricate the Fourier filter, wherein the substrate is substantially transparent to light from the specimen, and wherein the one or more pigments exhibit substantially no outgassing when illuminated by the light from the specimen; and
   a control subsystem configured to control the fabrication subsystem based on the image generated by the optical subsystem such that the patterned features formed on the substrate block the light reflected and diffracted from the structures on the specimen and allow light scattered from defects on the specimen to pass through the substrate.

24. The system of claim 23, wherein the fabrication subsystem comprises a print head configured to form the array of the patterned features on the substrate.

25. The system of claim 23, wherein the fabrication subsystem is further configured to form drops of the one or more pigments having a size of greater than about 500 dpi.

26. The system of claim 23, wherein the one or more pigments comprise one or more pigments that are curable by ultraviolet light.

27. The system of claim 23, further comprising a mask having known features formed thereon, wherein the control subsystem is further configured to calibrate the optical subsystem using the mask prior to imaging of the light in the Fourier plane.

28. The system of claim 23, wherein the light in the Fourier plane imaged by the optical subsystem comprises light reflected and diffracted from all structures formed on the specimen.

29. The system of claim 28, wherein the control subsystem is further configured to control the fabrication subsystem based on the image generated by the optical subsystem, diffraction orders of interest, a calibration factor, and tolerances of diffraction width.

30. The system of claim 23, wherein the control subsystem is further configured to control the fabrication subsystem to cause the patterned features to have apodization.

31. The system of claim 23, wherein the control subsystem is further configured to control the fabrication subsystem to cause the patterned features to have rough edges.

* * * * *